United States Patent [19]

Burke et al.

[11] Patent Number: 4,618,267
[45] Date of Patent: Oct. 21, 1986

[54] REMOTE TEMPERATURE-SET-POINT CONTROLLER

[75] Inventors: William F. Burke, Crest Hill; Alan L. Winiecki, Downers Grove, both of Ill.

[73] Assignee: The United States of America as represented by the United States Department of Energy, Washington, D.C.

[21] Appl. No.: 661,843

[22] Filed: Oct. 17, 1984

[51] Int. Cl.$^4$ .............................................. G01N 3/18
[52] U.S. Cl. ........................................ 374/50; 73/826; 374/46
[58] Field of Search ................... 374/46, 47, 48, 49, 374/50, 51, 52, 53, 54, 55, 56, 57; 73/826

[56] References Cited

U.S. PATENT DOCUMENTS

| | | | |
|---|---|---|---|
| 2,375,032 | 5/1945 | Parke et al. | 374/50 |
| 2,375,034 | 5/1945 | Semchyshen | 374/50 |
| 2,436,317 | 2/1948 | Manjoine | 374/49 |
| 2,685,195 | 8/1954 | Streblon | 374/47 |
| 3,034,718 | 5/1962 | Freitas et al. | |
| 3,100,253 | 8/1963 | O'Connor | 374/50 |
| 3,212,321 | 10/1965 | Kyle | 374/50 |
| 3,611,787 | 10/1971 | D'Annessa et al. | 374/50 |
| 4,295,360 | 10/1981 | Fountain | 374/49 |
| 4,320,870 | 8/1982 | Manor | 236/37 |
| 4,338,791 | 7/1982 | Stamp et al. | |
| 4,373,663 | 2/1983 | Hammer | 364/565 X |
| 4,393,718 | 7/1983 | Gebhard et al. | 374/49 |
| 4,411,306 | 10/1983 | Kabat | 165/12 |
| 4,421,268 | 12/1983 | Bassett et al. | 236/10 |

Primary Examiner—Daniel M. Yasich
Attorney, Agent, or Firm—William Lohff; Robert J. Fisher; Judson R. Hightower

[57] ABSTRACT

An instrument for carrying out mechanical strain tests on metallic samples with the addition of an electrical system for varying the temperature with strain, the instrument including opposing arms and associated equipment for holding a sample and varying the mechanical strain on the sample through a plurality of cycles of increasing and decreasing strain within predetermined limits, circuitry for producing an output signal representative of the strain during the tests, apparatus including a set point and a coil about the sample for providing a controlled temperature in the sample, and circuitry interconnected between the strain output signal and set point for varying the temperature of the sample linearly with strain during the tests.

10 Claims, 4 Drawing Figures

REMOTE TEMPERATURE-SET-POINT CONTROLLER

CONTRACTUAL ORIGIN OF THE INVENTION

The United States Government has rights in this invention pursuant to Contract No. W-31-109-ENG-38 between the U.S. Department of Energy and Argonne National Laboratory.

BACKGROUND OF THE INVENTION

This invention relates to a temperature control system for instruments which provide cyclic tests on metallic samples resulting in mechanical strain data, and more particularly to a temperature control system for varying the temperature of the sample during the test to provide conditions more similar to the actual process.

Existing instruments provide mechanical strain data on metallic samples to determine the number of cycles that a sample is capable of withstanding the mechanical load. This information is useful in designing various process equipment. However, in some instances, the variation in strain which occurs in the equipment is associated with a change in temperature. Normally thermal cycling reduces the ability of the sample to withstand the same number of cycles compared to those at a fixed temperature. Accordingly, modification of existing instruments is desirable to represent actual conditions.

Therefore, one object of the invention is a temperature control system for varying the temperature ($\Delta t$) of the sample with increasing strain ($\Delta s$) in a fully reversed strain cycle test. A second object is a temperature control system for adjusting the average test temperature prior to the test and changing the $\Delta t/\Delta s$ to provide a predetermined maximum test temperature. Another object is a temperature control system for providing a low cost circuit to accomplish the above objects.

SUMMARY OF THE INVENTION

Briefly, the temperature control system of the invention is provided for an instrument which produces mechanical strain data on a sample in a fully reversed strain cycle test, with the control system including temperature means for varying the temperature of the sample based on a variation in a temperature set point, means for producing an output signal corresponding to the strain at any point in the test, and circuit means for changing the set point linearly with changing strain on the sample. More specifically the circuit includes means for adjusting the set point for a starting temperature and means for adjusting the rate of change of temperature per unit change in strain to provide a predetermined maximum value of temperature which occurs with the maximum value of strain. Further the circuit includes means for reversing the rate of change so that a negative rate of change may be provided.

DETAILED DESCRIPTION OF THE PREFERRED EMBODIMENT

Figure 1:
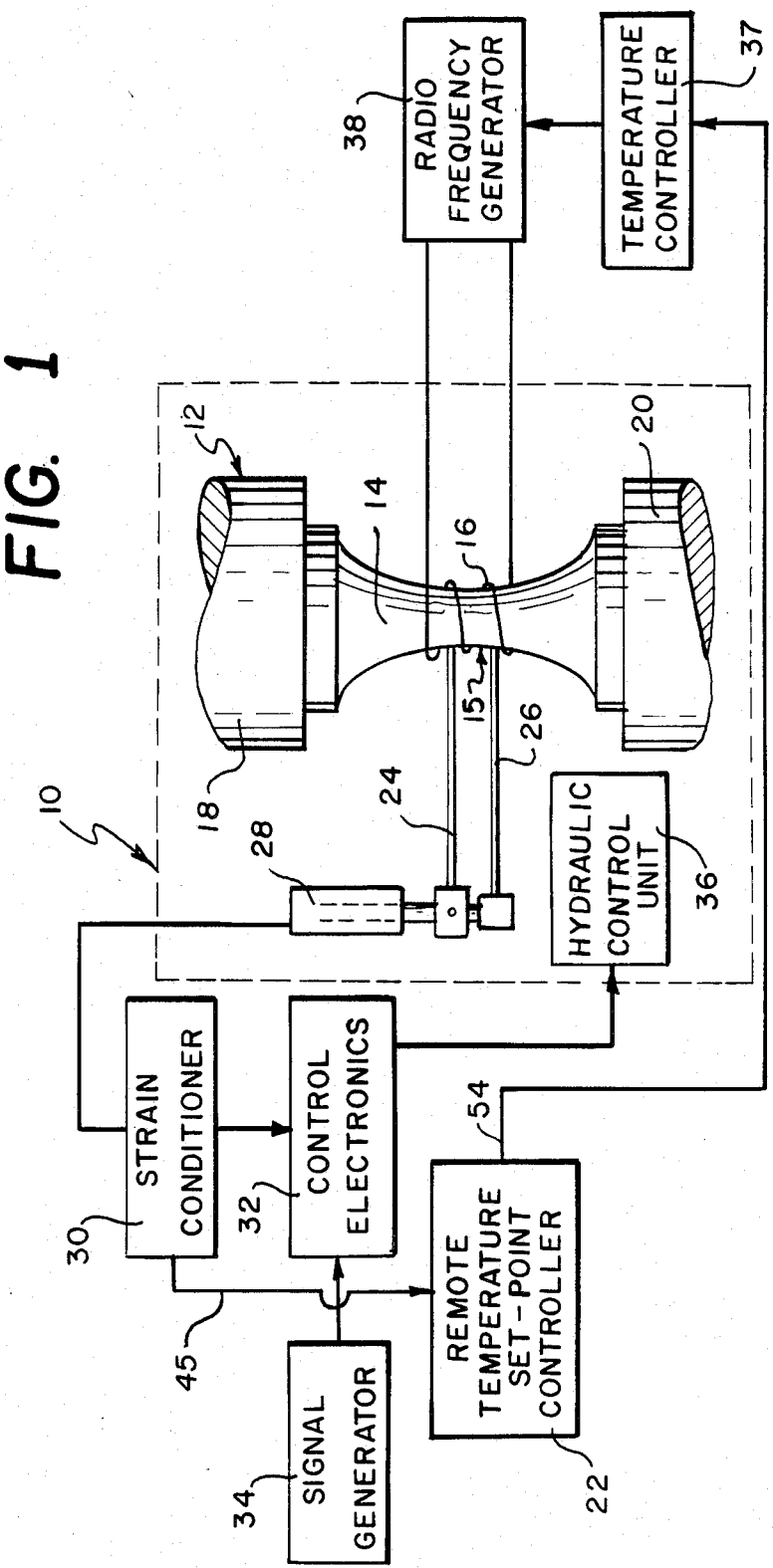
FIG. 1 is a schematic of an instrument for providing mechanical strain on a sample in a fully reversed cycle test to illustrate one embodiment of the invention.

As illustrated in FIG. 1, the test instrument 10 includes a fixture 12 for holding a sample 14 and a radio frequency electrical coil 16 about the sample for inducing a temperature in the sample. The fixture 12 includes a pair of opposing arms 18 and 20 which are coupled to sample 14 and forced apart by a conventional hydraulic actuator (not shown) in the instrument. As the section 15 of the sample between the arms 18 and 20 is increased in length, data representing the strain are provided as a measurement of the length or change of length. The temperature in the sample is set by set point means as illustrated by a remote temperature set-point controller 22 with the temperature set point being adjustable by an external signal from strain conditioner 30. In the test, the strain is changed between minimum and maximum values in a plurality of cycles until the sample fails by breakage, permanent distortion or the like.

In the operation of instrument 10, the increased length of sample 14 representing an increase in strain is measured by a pair of lever arms 24 and 26 with the increase being converted into a strain signal by a strain transducer 28. A strain conditioner 30 provides a first output signal to control electronics 32 which are further controlled by a signal generator 34. The control electronics 32 have an output used to provide a control of a hydraulic system 36 for moving the fixture arms 18 and 20 apart at a controlled rate as the strain is increased. The strain conditioner 30 further provides a second output signal representative of strain and used to control the set point signal in the remote temperature set-point controller 22. This controller 22 has an output which is fed to a known temperature controller 37 which controls the output of radio frequency generator 38. The output of radio frequency generator 38 is fed to electrical coil 16 which is coupled to sample 14 and provides a heat input to the sample 14.

Figure 4:
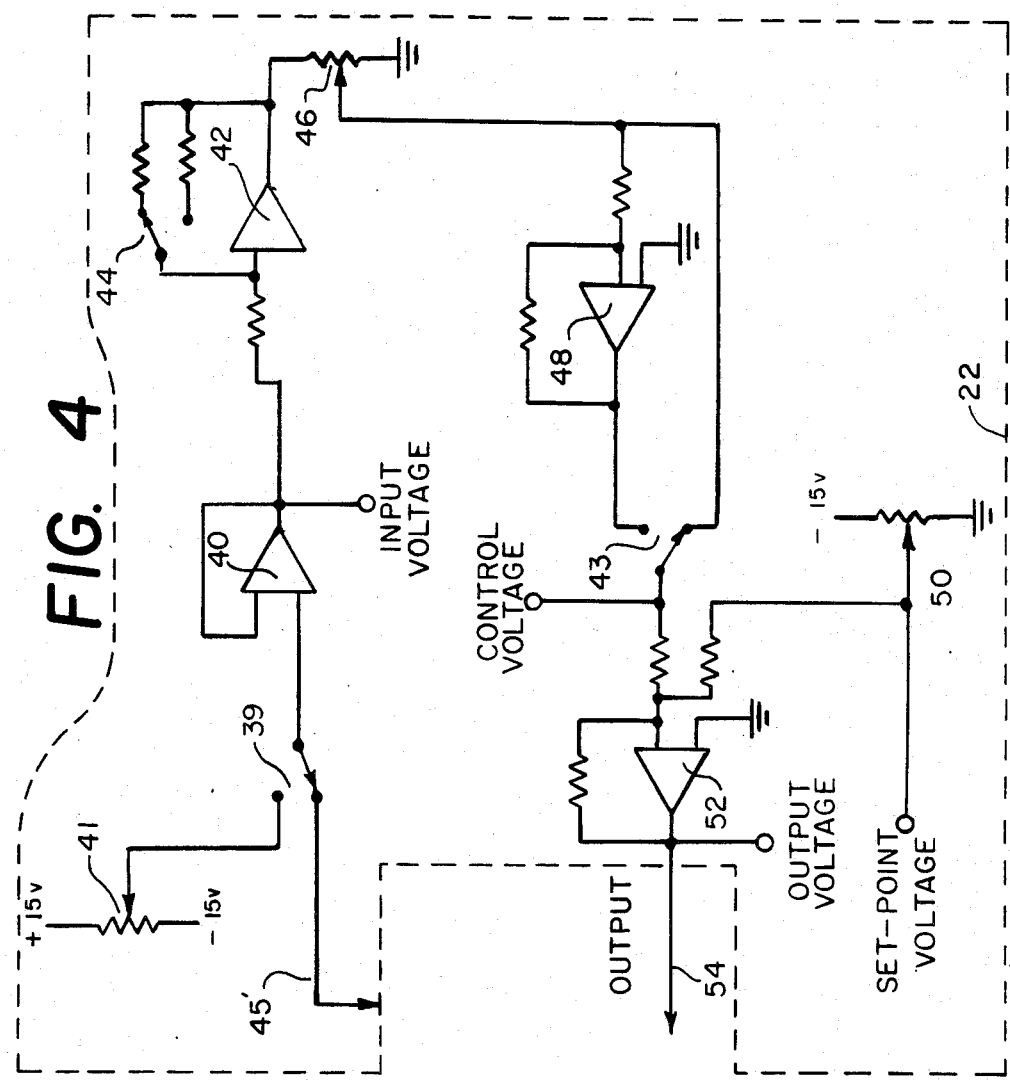
FIG. 4 is a schematic of the circuit with a temperature set point controller of FIG. 1 for adjusting the temperature of the sample to change the temperature with a change of strain.

As described previously, FIG. 1 represents a schematic of one embodiment of the invention with FIG. 4 being a schematic of the circuit of FIG. 1 for adjusting the temperature of the sample to change temperature with a change in strain. The circuit of FIG. 4 is identified with the remote temperature set-point controller 22 of FIG. 1 having an input signal 45 and output signal 54. Input signal 45 is representative of strain and is provided by strain conditioner 30 which also provides an output signal for controlling hydraulic control unit 36 through control electronics 32.

Figure 2:
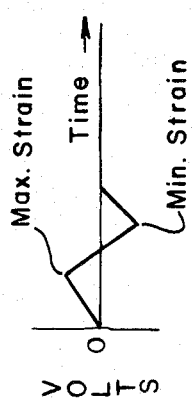
FIG. 2 is a graph of the change in strain versus time.
Figure 3:
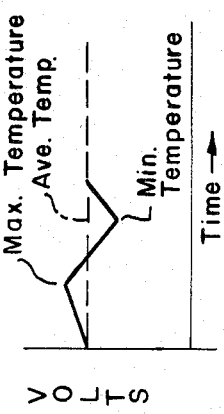
FIG. 3 is a graph of the change in temperature versus time.

FIGS. 2-3 illustrate the respective change in strain and the resultant temperature change versus time from the set-point controller. As illustrated, the value of strain varies between minimum and maximum values with the temperature being changed to vary linearly with strain.

As illustrated in FIGS. 1-4, the temperature control system includes means for adjusting the temperature set point used to control the sample temperature, means for providing a signal representative of the strain of the sample at any point in the test, and means interconnected between signal representing strain and the set point for varying the temperature based on a linear change in the strain of the sample. A strain output signal is provided by connecting the circuit to the strain conditioner 30 which provides a measurement of strain as an input signal for the circuit identified in FIG. 1 as the remote temperature set point controller 22. The input strain signal is buffered by amplifier 40 so that the input strain signal is isolated by a high impedance. Amplifier 42 in conjunction with switch 44 selects a gain factor of either 1 or 2. Pot 46 further selects another gain factor between 0 and 1. Amplifier 48, if the invert switch so selects, still further selects a gain factor of −1. The overall gain, by combining the effects of 42, 44, 46 and 48 is between −2.0 and +2.0. The set point pot 50, selects an average set point voltage. Summing amplifier 52 sums the output of 48 or 46 with 50 for output 54. The output temperature control signal is P3±P2 (1 or 2) (input strain signal) where P3 is the value of pot 50 and P2 is the value of pot 46 and the signal corresponds to the equation $$T = K_1 \pm K_2 S$$

where T is temperature, $K_1 = P_3$, $K_2 = P_2$, and S is strain. The output temperature set point control signal is then fed to the temperature controller 37. The average temperature is adjusted by resistance pot 50. The rate of change is provided by amplifier 42 via switch 44 and pot 46 so that a maximum temperature occurs with a maximum strain. The circuit also includes a switch 39 and pot 41 to pretest the control system and a second switch 43 to reverse the rate of change. Test points designated as "INPUT VOLTAGE", "CONTROL VOLTAGE", "OUTPUT VOLTAGE", and "SET-POINT VOLTAGE" are provided for test purposes.

The foregoing description of embodiments of the invention has been presented for purposes of illustration and description. It is not intended to be exhaustive or to limit the invention to the precise form disclosed, and obviously many modifications and variations are possible in light of the above teaching.

We claim:

1. A temperature control system for an instrument for providing mechanical strain data in a fully reversed cycle test on a metallic sample with the strain results being minimum and maximum values, the system comprising temperature means coupled to said sample for varying the temperature of the sample during the test including a set point means in a controlled device corresponding to a controlled temperature, means coupled to said sample for determining the value of strain during the test and providing an output signal representative of strain, and circuit means interconnected between the strain output and set point means for changing the set point linearly with changing values of strain output.

2. The system of claim 1 wherein the circuit means includes analog means for changing the temperature set point.

3. The system of claim 2 wherein the circuit means includes analog means for changing the temperature set point per unit change in strain as the strain is increased to a maximum value.

4. The system of claim 3 wherein the circuit means includes analog means for reversing the temperature set point change per unit change in strain.

5. The temperature control system of claim 3 wherein the analog means includes means for varying the temperature based on the equation $$T = K_1 \pm K_2 S$$

where T is temperature, $K_1$ and $K_2$ are constants, and S represents said output signal.

6. An instrument comprising sample means for holding a metallic sample and varying the mechanical strain on the sample through a plurality of cycles in which the strain is increased and decreased between limits, means interconnected with the sample means and coupled to said sample for producing an output signal representative of the strain during the cycling tests, temperature means coupled to said sample for varying the temperature of the sample during the test including a set point means in a controlled device corresponding to a controlled temperature, and circuit means interconnected between the strain output signal and set point for changing the set point linearly with changing values of the strain output signal.

7. The instrument of claim 6 wherein the circuit means includes analog means for changing the temperature set point.

8. The instrument of claim 7 wherein the circuit means includes analog means for changing the temperature set point per unit change in strain as the strain is increased to a maximum and decreased to a minimum.

9. The instrument of claim 8 wherein the circuit means includes analog means for reversing the temperature set point change per unit change in strain.

10. The instrument of claim 8 wherein the analog means includes means for varying the temperature based on the equation $$T = K_1 \pm K_2 S$$

where T is temperature, $K_1$ and $K_2$ are constants, and S represents a variable based on strain.

* * * * *